US007273603B2

(12) United States Patent
Schmidt

(10) Patent No.: US 7,273,603 B2
(45) **Date of Patent: *Sep. 25, 2007**

(54) HFC SOLUTION FORMULATIONS CONTAINING AN ANTICHOLINERGIC

(75) Inventor: Friedrich Schmidt, Ingelheim (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 39 days.

This patent is subject to a terminal disclaimer.

(21) Appl. No.: 10/882,494

(22) Filed: Jul. 1, 2004

(65) Prior Publication Data

US 2005/0008578 A1 Jan. 13, 2005

Related U.S. Application Data

(60) Provisional application No. 60/508,032, filed on Oct. 2, 2003.

(30) Foreign Application Priority Data

Jul. 11, 2003 (EP) .................................. 03015834

(51) Int. Cl.

*A61K 9/08* (2006.01)
*A61K 9/00* (2006.01)
*A61K 31/46* (2006.01)
*A01N 43/90* (2006.01)
*C07D 487/10* (2006.01)

(52) U.S. Cl. ........................... 424/45; 514/291; 546/91

(58) Field of Classification Search .................. 424/45; 514/291, 304; 546/91, 130

See application file for complete search history.

(56) References Cited

U.S. PATENT DOCUMENTS

2003/0089369 A1* 5/2003 Lewis et al. ........... 128/200.23

* cited by examiner

*Primary Examiner*—Johann R. Richter
*Assistant Examiner*—James H Alstrum-Acevedo
(74) *Attorney, Agent, or Firm*—Michael P. Morris; Mary-Ellen M. Devlin; Wendy Petka

(57) ABSTRACT

An aerosol solution formulation comprising:

(a) a salt of formula 1

1

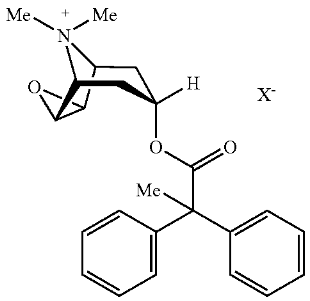

wherein $X^-$ is an anion (b) an HFC propellant;

(c) a cosolvent; and (d) an inorganic or an organic acid, wherein the concentration of the acid is in a range that corresponds with a pH range of 2.5 to 5.5 in aqueous solution.

22 Claims, No Drawings

HFC SOLUTION FORMULATIONS CONTAINING AN ANTICHOLINERGIC

RELATED APPLICATIONS

This application claims benefit of U.S. Ser. No. 60/508,032, filed on Oct. 2, 2003, and claims priority to European Application No. 03 015 834.9, filed Jul. 11, 2003, each of which is hereby incorporated by reference in its entirety.

FIELD OF THE INVENTION

This invention relates to stable pharmaceutical solution formulations suitable for aerosol administration containing an anticholinergic of formula 1

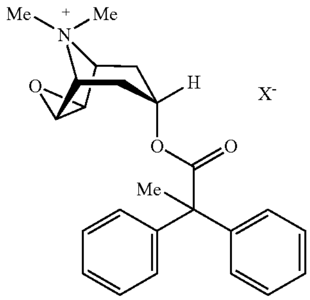

1 wherein $X^-$ is a pharmaceutically acceptable anion. More particularly, this invention relates to stable pharmaceutical solution formulations suitable for aerosol administration containing an anticholinergic of formula 1 in an environmentally safe hydrofluorocarbon (HFC) as a propellant, together with an organic compound as a cosolvent wherein either an inorganic acid or an organic acid is added to the aerosol solution formulation.

BACKGROUND OF THE INVENTION

The compounds of formula 1 are known from WO 02/32899 (corresponding to U.S. Patent Application Pub. No. US 2002/0115680, which is hereby incorporated by reference). They represent highly effective anticholinergics with a long-lasting activity which can be used to treat respiratory complaints, particularly chronic obstructive pulmonary disease (COPD) and asthma.

For treating the abovementioned complaints, it is useful to administer the active substance by inhalation. In addition to the administration of broncholytically active compounds in the form of inhalable powders containing the active substance, the administration of active substances can also occur in form of hydrofluorocarbon containing aerosol solution formulations.

The administration of aerosol formulations of medicaments by means of pressurized, metered-dose inhalers (MDIs) is used widely in therapy, such as in the treatment of obstructive airway diseases and asthma. Compared with oral administration, inhalation provides more rapid onset of action while minimizing systemic side effects. Aerosol formulations can be administered by inhalation through the mouth or topically by application to the nasal mucosa.

Formulations for aerosol administration using MDIs can be solutions or suspensions. Solution formulations offer the advantage of being homogeneous in nature with the medicament and excipient completely dissolved in the propellant vehicle. Solution formulations also obviate physical stability problems associated with suspension formulations and thus assure more consistent uniform dosage administration while also eliminating the need for surfactants.

The administration of aerosol solution formulations using MDIs is dependent upon the propulsive force of the propellant system used in its manufacture. Traditionally, the propellant comprised a mixture of chlorofluorocarbons (CFCs) to provide the desired solubility, vapor pressure, and stability of the formulation. However, since it has been established in recent years that CFCs are environmentally harmful because they contribute to the depletion of the Earth's ozone layer, it is desirable to substitute environmentally safe hydrofluorocarbon (HFC) propellants or other nonchlorinated propellants for environmentally harmful CFC propellants in aerosol inhalation formulations. For example, U.S. Pat. No. 4,174,295, discloses the use of propellant systems consisting of combinations of HFCs, which may also contain a saturated hydrocarbon component, suitable for application in the fields of home products such as hair lacquers, anti-perspiration products, perfumes, deodorants, paints, insecticides, and the like.

It is known in the art that certain HFCs have properties suitable for use as propellants for the aerosol administration of medicaments. For example, European Patent Application No. 0 372 777 describes the use of 1,1,1,2-tetrafluoroethane (HFC-134(a)) in combination with at least one "adjuvant" (a compound having a higher polarity than the HFC-134(a)) and a surface active agent to prepare suspension and solution formulations of medicaments suitable for administration by the aerosol route. Also, PCT Application No. WO 91/11496 discloses the use of 1,1,1,2,3,3,3-heptafluoropropane (HFC-227), optionally mixed with other propellant components, for use in preparing suspension aerosol formulations of medicaments.

U.S. Pat. Nos. 2,868,641 and 3,282,781 disclose aerosol compositions comprising a medicament (epinephrine or isoproterenol HCl), a cosolvent, a propellant and ascorbic acid as antioxidant. European Patent EP 673 240 B1 proposes the addition of acids to medicinal aerosol formulations in order to provide for the stabilization of the medicament.

DESCRIPTION OF THE INVENTION

The term "aerosol solution formulation" means a pharmaceutical formulation of a medicament suitable for aerosol administration wherein the medicament and excipients are completely dissolved.

The term "stabilized aerosol solution formulation" means an aerosol solution formulation which exhibits substantial chemical stability over time.

The present invention provides stabilized aerosol solution formulations comprising a salt of formula 1

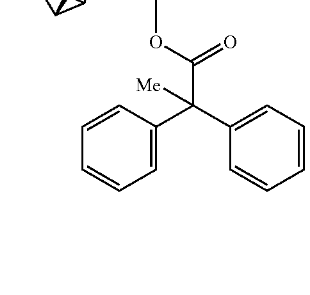

1 wherein:

$X^-$ denotes an anion, preferably an anion selected from the group consisting of chloride, bromide, iodide, sulfate, phosphate, methanesulfonate, nitrate, maleate, acetate, citrate, fumarate, tartrate, oxalate, succinate, benzoate, and p-toluenesulfonate, an HFC propellant, a cosolvent, and an inorganic or an organic acid, characterized in that the concentration of the acid is in a range that corresponds with a pH range of 2.5 to 5.5 in aqueous solution.

In a preferred embodiment of the invention, the aerosol solution formulations contain those salts of formula 1 wherein $X^-$ denotes an anion with a single negative charge selected from among the chloride, bromide, 4-toluenesulfonate, and methanesulfonate, preferably bromide.

In another preferred embodiment of the invention, the aerosol solution formulations contain those salts of formula 1 wherein $X^-$ denotes an anion with a single negative charge selected from among the chloride, bromide, and methanesulfonate, preferably bromide.

In a yet another preferred embodiment of the invention, the aerosol solution formulations contain the salt of formula 1 wherein $X^-$ denotes bromide.

The salts 1 may possibly be present in the form of their solvates or hydrates.

In preferred aerosol solution formulations according to the invention, the concentration of the acid is in a range that corresponds with a pH range of 3.0 to 5.0, more preferred 3.5 to 4.5, in aqueous solution.

A small amount of water (up to about 5%, preferably up to about 3% by weight) may also be present in the propellant/cosolvent system.

Particular preferred the aerosol solution formulations according to the invention contain one or more, preferably one, salts of formula 1 as the single active ingredient.

Within the scope of the present invention, any reference to the compound 1' is to be regarded as a reference to the pharmacologically active cation of the following formula 1' contained in the salts 1:

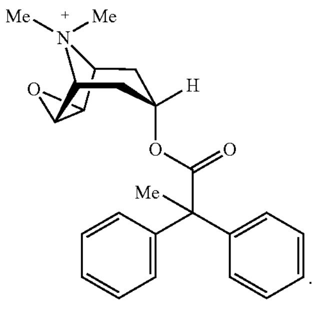

1'

The aerosol solution formulation according to the invention preferably contains 0.00008% to 4%, preferably 0.0004% to 1.6%, more preferably 0.0008% to 0.8% of the pharmacologically active cation 1'.

If the particularly preferred salt 1, the bromide, is used, the aforementioned amounts of the cation 1 correspond to 0.000097% to 4.8%, preferably 0.00048% to 1.94%, more preferably 0.00097% to 0.97%, of 1 (in form of the bromide).

Suitable HFC propellants are those which, when mixed with the cosolvent(s), form a homogeneous propellant system in which a therapeutically effective amount of the medicament can be dissolved. The HFC propellant must be toxicologically safe and must have a vapor pressure which is suitable to enable the medicament to be administered using a pressurized MDI. Additionally, the HFC propellant must be compatible with the components of the MDI device (such as containers, valves, and sealing gaskets, etc.) which is employed to administer the medicament. Preferred HFC propellants are 1,1,1,2-tetrafluoroethane (HFC-134(a)) and 1,1,1,2,3,3,3,-heptafluoropropane (HFC-227). HFC-134(a) is particularly preferred. Other examples of HFC propellants are HFC-32 (difluoromethane), HFC-143(a) (1,1,1-trifluoroethane), HFC-134 (1,1,2,2-tetrafluoroethane), and HFC-152a (1,1-difluoroethane).

It will be apparent to those skilled in the art that nonhalogenated hydrocarbon propellants may be used in place of the HFC propellants in the present invention. Examples of nonhalogenated hydrocarbons are saturated hydrocarbons, including propane, n-butane, and isobutane, and ethers, including diethyl ether.

It will also be apparent to those skilled in the art that, although the use of a single HFC propellant is preferred, a mixture of two or more HFC propellants, or a mixture of at least one HFC propellant and one or more non-CFC propellants, may be employed in the aerosol solution formulation of the present invention.

The acid in the formulations according to the invention may be any inorganic or mineral acid, for example, hydrochloric acid, sulfuric acid, nitric acid, or phosphoric acid, or the like. Of the aforementioned acids, hydrochloric acid and phosphoric acid are of particular interest. The acid may also be selected from the group of acids known to those skilled in the art as organic acids, which are in most cases considered to be weak acids relative to the inorganic acids. Representative of this group and preferred in this invention are ascorbic acid, citric acid, lactic acid, malic acid, benzoic acid, and tartaric acid. According to this invention, citric acid and ascorbic acid are the most preferred organic acids.

The formulations according to the invention can be prepared in analogy to methods known in the art.

If desired, pharmaceutically acceptable excipients can be included in the aerosol solution formulations of the present invention. For example, a soluble surface active agent can be added in order to improve the performance of valve systems employed in the MDI devices used for the aerosol administration of the formulations. Examples of preferred surface active agents are sorbitan trioleate, lecithin, isopropylmyristate, ethoxylated glycerol trioleates, and alkyl polyglycosides. Other suitable lubricants are well known in the art (see, for example, European Patent Application No. 0 372 777). Other excipients are: (a) antioxidants, for example, ascorbic acid and tocopherol; (b) taste masking agents, for example, menthol, sweeteners, and artificial or natural flavors; and (c) pressure modifying agents, for example, n-pentane, isopentane, neopentane, and n-hexane.

Examples of cosolvents applicable within the formulations according to the invention are: alcohols, for example, ethyl alcohol, isopropyl alcohol, and benzyl alcohol; glycols for example, propylene glycol, polyethylene glycols, polypropylene glycols, glycol ethers, and block copolymers of oxyethylene and oxypropylene; and other substances, for example, glycerol, polyoxyethylene alcohols, polyoxyethylene fatty acid esters, and glycofurols (for example, glycofurol 75).

Examples of cosolvents that may be inert to interaction with the medicament(s) are hydrocarbons, for example, n-propane, n-butane, isobutane, n-pentane, isopentane, neopentane, and n-hexane; and ethers, for example, diethyl ether. A preferred cosolvent according to this invention is ethyl alcohol (ethanol).

The amount of cosolvent is preferably in the range of 5% to 50% (w/w) of the total composition. More preferably, the amount of cosolvent in the formulation according to the invention is in the range of 10% to 40% (w/w), preferably in the range of 15% to 30%.

As mentioned hereinbefore, the formulations according to the invention may contain water. One preferred embodiment of the invention pertains to formulations that contain water in an amount of up to 5% (w/w), preferably of up to 3% (w/w). Another preferred embodiment of the invention is directed to formulations that do not contain any water. In these water-free formulations the amount of cosolvent is preferably in the range of about 20% to 50% (w/w), more preferably in the range of about 30% to 40% (w/w).

The formulations according to the invention can be administered with metered dose inhalers known in the art.

In another aspect the invention is directed to the use of an aerosol solution formulation as described hereinbefore for the manufacture of a medicament for the treatment of respiratory complaints, particularly COPD and asthma.

In yet another aspect the invention is directed to a method for treatment of respiratory complaints, such as in particular COPD or asthma, characterized by the administration of an aerosol solution formulation as described hereinbefore.

The following Examples serve to illustrate the present invention further without restricting its scope to the embodiments provided hereinafter by way of example.

I. FORMULATION EXAMPLES

| Component | Concentration [% w/w] |
|---|---|
| A) | |
| 1 (wherein $X^-$ is bromide) | 0.2 |
| Ethanol abs. (USP) | 25 |
| Water (purified, USP) | 1.0 |
| Citric acid (USP) | 0.003 |
| HFC-134a | 73.797 |
| B) | |
| 1 (wherein $X^-$ is bromide) | 0.1 |
| Ethanol abs. (USP) | 20.0 |
| Aqueous HCl 0.01 mol/l (USP) | 2.0 |
| HFC-134a | 77.9 |
| C) | |
| 1 (wherein $X^-$ is bromide) | 0.1 |
| Ethanol abs. (USP) | 15.0 |
| Water (purified, USP) | 2.0 |
| Citric acid (USP) | 0.004 |
| HFC-227 | 82.896 |
| D) | |
| 1 (wherein $X^-$ is bromide) | 0.2 |
| Ethanol abs. (USP) | 30.0 |
| Water (purified, USP) | 1.0 |
| Ascorbic acid (USP) | 0.005 |
| HFC-134a | 68.795 |
| E) | |
| 1 (wherein $X^-$ is bromide) | 0.05 |
| Ethanol abs. (USP) | 40.0 |
| citric acid (USP) | 0.004 |
| HFC-227 | 59.991 |

The aforementioned formulations can be prepared by conventional methods known in the state of the art.

What is claimed is:

1. An aerosol solution formulation comprising:

(a) a salt of formula 1

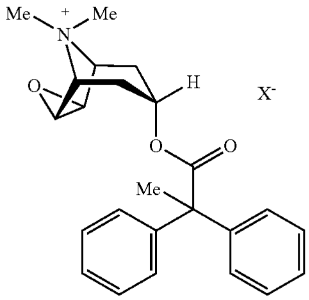

1 wherein $X^-$ is an anion (b) an HFC propellant;

(c) a cosolvent; and (d) an inorganic or an organic acid, wherein the concentration of the acid is in a range that corresponds with a pH range of 2.5 to 5.5 in aqueous solution.

2. The aerosol solution formulation according to claim 1, wherein $X^-$ is chloride, bromide, iodide, sulfate, phosphate, methanesulfonate, nitrate, maleate, acetate, citrate, fumarate, tartrate, oxalate, succinate, benzoate, or p-toluenesulfonate.

3. The aerosol solution formulation according to claim 1, wherein the aerosol solution formulation contains 0.0000800% to 400% of the pharmacologically active cation of formula 1'

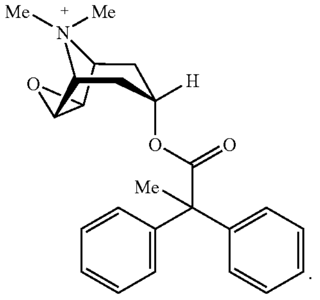

1'

4. The aerosol solution formulation according to claim 1, wherein the HFC propellant is HFC-134(a), HFC-227, HFC-32, HFC-143(a), HFC-134, HFC-152a, or a mixture thereof.

5. The aerosol solution formulation according to claim 2, wherein the HFC propellant is HFC-134(a), HFC-227, HFC-32, HFC-143(a), HFC-134, HFC-152a, or a mixture thereof.

6. The aerosol solution formulation according to claim 3, wherein the HFC propellant is HFC-134(a), HFC-227, HFC-32, HFC-143(a), HFC-134, HFC-152a, or a mixture thereof.

7. The aerosol solution formulation according to claim 1, wherein the acid is hydrochloric acid, sulfuric acid, nitric acid, or phosphoric acid.

8. The aerosol solution formulation according to claim 2, wherein the acid is hydrochloric acid, sulfuric acid, nitric acid, or phosphoric acid.

9. The aerosol solution formulation according to claim 3, wherein the acid is hydrochloric acid, sulfuric acid, nitric acid, or phosphoric acid.

10. The aerosol solution formulation according to claim 1, wherein the acid is ascorbic acid, citric acid, lactic acid, malic acid, benzoic acid, or tartaric acid.

11. The aerosol solution formulation according to claim 2, wherein the acid is ascorbic acid, citric acid, lactic acid, malic acid, benzoic acid, or tartaric acid.

12. The aerosol solution formulation according to claim 3, wherein the acid is ascorbic acid, citric acid, lactic acid, malic acid, benzoic acid, or tartaric acid.

13. The aerosol solution formulation according to claim 1, wherein the aerosol solution formulation contains water in an amount of up to about 5%.

14. The aerosol solution formulation according to claim 2, wherein the aerosol solution formulation contains water in an amount of up to about 5%.

15. The aerosol solution formulation according to claim 3, wherein the aerosol solution formulation contains water in an amount of up to about 5%.

16. The aerosol solution formulation according to claim 1, wherein the cosolvent is an alcohol, glycol, glycol ether, block copolymer of oxyethylene and oxypropylene, glycerol, polyoxyethylene alcohol, polyoxyethylene fatty acid ester, or glycofurol.

17. The aerosol solution formulation according to claim 2, wherein the cosolvent is an alcohol, glycol, glycol ether, block copolymer of oxyethylene and oxypropylene, glycerol, polyoxyethylene alcohol, polyoxyethylene fatty acid ester, or glycofurol.

18. The aerosol solution formulation according to claim 3, wherein the cosolvent is an alcohol, glycol, glycol ether, block copolymer of oxyethylene and oxypropylene, glycerol, polyoxyethylene alcohol, polyoxyethylene fatty acid ester, or glycofurol.

19. The aerosol solution formulation according to claim 1, wherein the cosolvent is present in an amount in the range of 5% to 50% (w/w).

20. The aerosol solution formulation according to claim 16, wherein the cosolvent is present in an amount in the range of 5% to 50% (w/w).

21. The aerosol solution formulation according to claim 17, wherein the cosolvent is present in an amount in the range of 5% to 50% (w/w).

22. The aerosol solution formulation according to claim 18, wherein the cosolvent is present in an amount in the range of 5% to 50% (w/w).

* * * * *